(12) United States Patent
Ronen et al.

(10) Patent No.: US 9,345,438 B2
(45) Date of Patent: May 24, 2016

(54) WEANING FROM VENTILATION USING CAPNOGRAPHY

(71) Applicant: ORIDION MEDICAL 1987 LTD., Jerusalem (IL)

(72) Inventors: Michal Ronen, Bet-Elazari (IL); Sharon Einav, Zur Hadassah (IL); Keren Davidpur, Modi'in-Maccabim-Reut (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 147 days.

(21) Appl. No.: 14/188,069

(22) Filed: Feb. 24, 2014

(65) Prior Publication Data

US 2014/0171818 A1 Jun. 19, 2014

Related U.S. Application Data

(63) Continuation of application No. 13/703,162, filed as application No. PCT/IL2011/000453 on Jun. 9, 2011, now Pat. No. 8,695,596.

(60) Provisional application No. 61/353,243, filed on Jun. 10, 2010.

(51) Int. Cl.

| A61B 5/083 | (2006.01) |
|---|---|
| A61B 5/08 | (2006.01) |
| A61M 16/00 | (2006.01) |
| A61B 5/00 | (2006.01) |
| A61M 16/08 | (2006.01) |

(52) U.S. Cl.
CPC .............. *A61B 5/7282* (2013.01); *A61B 5/082* (2013.01); *A61B 5/0836* (2013.01); *A61B 5/4836* (2013.01); *A61B 5/4848* (2013.01); *A61B 5/7264* (2013.01); *A61B 5/7275* (2013.01); *A61M 16/0051* (2013.01); *A61M 16/0069* (2014.02); *A61M 16/085* (2014.02); *A61M 2230/432* (2013.01)

(58) Field of Classification Search
CPC ............ A61B 5/00; A61B 5/08; A61B 5/082; A61B 5/083; A61B 5/0836; A61B 5/4836; A61B 5/4848; A61B 5/7264; A61B 5/7275; A61B 5/7282; A61M 16/00; A61M 16/0051; A61M 16/0069; A61M 16/085; A61M 2016/085; A61M 2230/432
USPC ............. 128/200.24, 204.18, 204.21, 204.23; 600/531, 532
See application file for complete search history.

(56) References Cited

U.S. PATENT DOCUMENTS

| 5,103,814 | A | 4/1992 | Maher | |
|---|---|---|---|---|
| 6,273,088 | B1 * | 8/2001 | Hillsman | A61M 16/00 128/204.18 |
| 2002/0082511 | A1 * | 6/2002 | Carlebach | A61B 5/0836 600/529 |
| 2007/0240718 | A1 | 10/2007 | Daly | |
| 2008/0178882 | A1 | 7/2008 | Christopher | |
| 2008/0228096 | A1 | 9/2008 | Jaffe | |

* cited by examiner

*Primary Examiner* — Annette Dixon
(74) *Attorney, Agent, or Firm* — Rodney J. Fuller; Booth Udall Fuller, PLC

(57) ABSTRACT

Devices and systems for monitoring weaning of a subject from a respiratory ventilator including a processing logic configured to characterize distinct patterns in a series of $CO_2$ waveforms, the distinct patterns indicative of the effectiveness of a weaning process; and to provide an indication relating to the effectiveness of the weaning process.

9 Claims, 9 Drawing Sheets

WEANING FROM VENTILATION USING CAPNOGRAPHY

CROSS-REFERENCE TO RELATED APPLICATIONS

This application is a continuation of U.S. application Ser. No. 13/703,162, filed Dec. 10, 2012 (now issued as U.S. Pat. No. 8,695,596), which is the U.S. National Stage of International Application No. PCT/IL2011/000453, filed Jun. 9, 2011, which claims the benefit of U.S. Provisional Application No. 61/353,243, filed Jun. 10, 2010, the contents of each of which are herein expressly incorporated by reference for all purposes.

FIELD OF THE INVENTION

Embodiments of the invention are related to the use of capnography in weaning a patient from a ventilator.

BACKGROUND

Mechanical ventilatory support is widely accepted as an effective form of therapy and means for treating patients with respiratory failure. The early generation of mechanical ventilators, prior to the mid-1960s, were designed to support alveolar ventilation and to provide supplemental oxygen for those patients who were unable to breathe on their own. Since that time, mechanical ventilators have become more sophisticated and complicated in response to increasing understanding of lung pathophysiology. For example, CPAP (Continuous Positive Airway Pressure), BiPAP (Bilevel Positive Airway Pressure) and SIMV (Synchronized Intermittent Mandatory Ventilation) are effective in preventing need for intubation and also decreasing mortality in patients with acute respiratory failure.

Even though the ventilator technology is constantly improving, ventilator dependence is still a serious medical and economic problem. It is well known that severe and sometimes lethal complications may develop the longer a patient is on ventilator support. In addition, as ventilator therapy is provided in specialized and very expensive Intensive Care Unit environments, there is a need to minimize ventilator dependency. Weaning the patients from artificial ventilation is among the most difficult challenges of the regarding intensive care ventilation.

Prior art ventilator weaning monitoring methods are not efficient enough and are often depending on subjective impressions of clinical fatigue or distress and/or arterial blood gas derangements that of necessity measure failure after the failure has already developed. More modem monitoring techniques such as the ratio of Tidal Volume to Respiratory Rate are still relatively crude indices of weaning performance. Weaning from ventilator dependency is potentially hazardous due to unexpected precipitous ventilatory failure, and early warning by appropriate monitoring means is imperative for patient safety. Further, controlled stress of weakened respiratory muscles is imperative in order to recondition these muscles, but in addition to not over-stress these recovering muscles and therefore cause further damage. It is often difficult to safely define the proper degree of weaning stress clinically.

There is thus a need in the art for systems, devices and methods that would allow monitoring the constantly changing condition of a patient undergoing weaning from ventilation.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

In accordance with some aspects of the invention, systems, devices, and methods are provided, which facilitate the monitoring the effectiveness and progression of a weaning process using data related to the level of $CO_2$ in the expired breath of a ventilated patient.

In accordance with some embodiments of the invention, it was surprisingly found that certain characteristics or combination of characteristics relating to $CO_2$ waveform(s) of the expired breath of a patient are indicative to how well the weaning process is progressing. Characteristics related to $CO_2$ waveform(s) may include, for example, $CO_2$ waveform characteristics, characteristics or behavior of groups of $CO_2$ waveforms, time dependent behavior of the $CO_2$ waveforms, the frequency of appearance of certain characteristics, the ratios between certain characteristics or any combination thereof.

In accordance with some embodiments of the invention, there is provided a method for monitoring a respiratory patient to evaluate respiratory ventilator weaning (and/or train the patient for respiratory ventilator weaning), the method comprising characterizing one or more $CO_2$ waveforms obtained from expired breath of the respiratory patient (for example, detecting distinct patterns such as "sigh events", "spike events" and "pools" among "regular" $CO_2$ waveforms, see FIG. 1-3 and the "Detailed Description section) and evaluating respiratory ventilator weaning of the patient. The method may further include providing a signal to the ventilator at least partially based on the characterized one or more $CO_2$ waveforms and thus inducing a change of one or more parameters of the ventilator (for example, changing the level of support to the ventilation, allowing the patient to rest from the weaning attempts, changing the mode/program of weaning, etc.).

In accordance with some embodiments of the invention, there is provided a device for monitoring a respiratory patient to evaluate respiratory ventilator weaning (and/or train the patient for respiratory ventilator weaning), the device comprising:

a capnograph configured to provide one or more $CO_2$ waveforms;

processing logic configured to: (a) characterize the one or more $CO_2$ waveforms obtained by the capnograph (for example, detecting distinct patterns in the $CO_2$ waveforms, such as, "sigh events", "spike events" and "pools" among "regular" $CO_2$ waveforms, see FIG. 1-3 and the "Detailed Description section); and (b) provide a signal to the ventilator at least partially based on the characterized one or more $CO_2$ waveforms thereby induce a change of one or more parameters of the ventilator (for example, changing the level of support to the ventilation, allowing the patient to rest from the weaning attempts, changing the mode/program of weaning, etc.).

The prevalence and frequency of the waveforms characteristics, such as the above mentioned events as an indicator may be different for different ventilator modes. In other words, depending on the ventilator mode the event (for example, "sigh event") frequency may have a different meaning. One could also perform coordinated changes in the ventilator parameters/modes (for example, reductions of pressure support) and evaluate the consequent change in event pattern and accordingly continue or stop the process.

The processing logic may be further configured to provide the signal to the ventilator based on other parameters, in addition to the characteristics of the CO2 waveforms. Such parameters may include general patient parameters, such as age, medical condition, medical history, medications or any other parameter. The parameters may also include respiratory related parameters such as respiration rate, tidal volumes, minute ventilation (the total lung ventilation per minute), inspiration rate and expiration rate at ambient pressure in the absence of ventilator assistance, ventilator mode, ventilator setup parameters or any other parameter.

In accordance with some embodiments of the invention, there is provided a method for monitoring weaning of a subject from a respiratory ventilator, the method comprising characterizing distinct patterns in a series of $CO_2$ waveforms obtained from expired breath of a subject undergoing respiratory ventilation weaning, wherein said distinct patterns are indicative to the effectiveness of a weaning process and wherein said distinct patterns are selected from a group consisting of "sigh events", "spike events" and "pools" and providing an indication relating to the effectiveness of the weaning process.

The method may further include providing a signal to a ventilator at least partially based on the characterized distinct patterns in the series of $CO_2$ waveforms and thus inducing a change in one or more parameters of the ventilator.

In accordance with some embodiments of the invention, there is provided a device for monitoring weaning of a subject from a respiratory ventilator, the device comprising: processing logic configured to characterize distinct patterns in the series of $CO_2$ waveforms, wherein said distinct patterns are indicative to the effectiveness of a weaning process and wherein said distinct patterns are selected from a group consisting of "sigh events", "spike events" and "pools", wherein said processing logic is further configured to provide an indication relating to the effectiveness of the weaning process.

In accordance with some embodiments of the invention, there is provided a system for monitoring weaning of a subject from a respiratory ventilator, the system comprising: a capnograph configured to provide a series of $CO_2$ waveforms obtained from expired breath of a subject undergoing respiratory ventilation weaning; and processing logic configured to characterize distinct patterns in the series of $CO_2$ waveforms, wherein said distinct patterns are indicative to the effectiveness of a weaning process and wherein said distinct patterns are selected from a group consisting of "sigh events", "spike events" and "pools", wherein said processing logic is further configured to provide an indication relating to the effectiveness of the weaning process.

The change in one or more parameters of the ventilator may include a change in the level of support to the ventilation, allowing the patient to rest from weaning attempts, changing a mode/program of weaning or any combination thereof.

Providing a signal to the ventilator may further be based on one or more additional parameters selected from the group consisting of: age of the subject, medical condition of the subject, medical history of the subject and medications administered to the subject.

Providing a signal to the ventilator may further be based on one or more additional parameters selected from the group consisting of: respiration rate, tidal volumes, minute ventilation (the total lung ventilation per minute), inspiration rate and expiration rate at ambient pressure in the absence of ventilator assistance, ventilator mode and ventilator setup parameters.

Characterizing distinct patterns in a series of $CO_2$ waveforms may include segmenting the series of $CO_2$ waveforms into breaths (waveforms), and calculating for each breath one or more features.

The one or more features ay include: area under the curve (AUC), breath duration (inhalation, expiration or both), I to E ratio, maximal $CO_2$ value, minimal $CO_2$ value or any combination thereof.

Characterizing distinct patterns in the series of $CO_2$ waveforms may include determining the extent and/or frequency of appearance of said distinct patterns. Characterizing distinct patterns in the series of $CO_2$ waveforms may include determining the ratios between the distinct patterns.

The processing logic may further be configured to provide a signal to a ventilator at least partially based on the characterized distinct patterns in the series of $CO_2$ waveforms and thus inducing a change in one or more parameters of the ventilator.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

DETAILED DESCRIPTION

In accordance with some embodiments of the invention, certain types of distinct breathing patterns (characteristics) in data obtained from ventilated patients during weaning process were found and evaluated.

According to some embodiments, the $CO_2$ signal obtained from expired air of a subject was segmented into breaths (waveforms), and one or more features for each breath were calculated. Example of such features include area under the curve (AUC), breath duration (inhalation, expiration or both), I to E ratio (the ratio between inhalation to expiration in a breath), maximal $CO_2$ value, minimal $CO_2$ value, presence of small "dip(s)" in the waveform plateau or in the inhalation part of the breath (a dip in a waveform may be due to breathing effort that the ventilation does not capture), and other features.

The extent and/or frequency of appearance of these features may, over time, create certain patterns. According to some embodiments, these patterns may be indicative to the effectiveness of a weaning process. Three patterns were determined by their relative value of a feature or values of a set of features (as discussed herein according to some embodiments) compared to a pre-defined base-line or to an average or median feature value before weaning started (for example, when full ventilation was still applied) or to an average or median feature value obtained during a specific time period (for example the last X hours, such as 2-10, 12 to 24). The following three patterns were determined:

1) Sigh Events: breaths with relatively large AUC (for example, compared to a an average or median AUC value before weaning started or to the average or median AUC value obtained during a specific time period) or relatively high breath duration (for example, compared to an average or median breath duration value before weaning started or to an average or median breath duration value obtained during a specific time period) or any other typical feature.

2) Spike Events: breaths with very small AUC (for example, compared to a an average or median AUC value before weaning started or to the average or median AUC value obtained during a specific time period) or relatively small breath duration and/or relatively low maximal $CO_2$ or any other typical feature (for example, compared to the respective feature value before weaning started or to an average or median respective feature value obtained during a specific time period).

3) Pools: group of breaths with relatively low AUC (for example, compared to a an average or median AUC value before weaning started or to the average or median AUC value obtained during a specific time period) or low maximal $CO_2$ or low breath duration or any other typical feature (for example, compared to the respective feature value before weaning started or to an average or median respective feature value obtained during a specific time period).

Figure 1A:
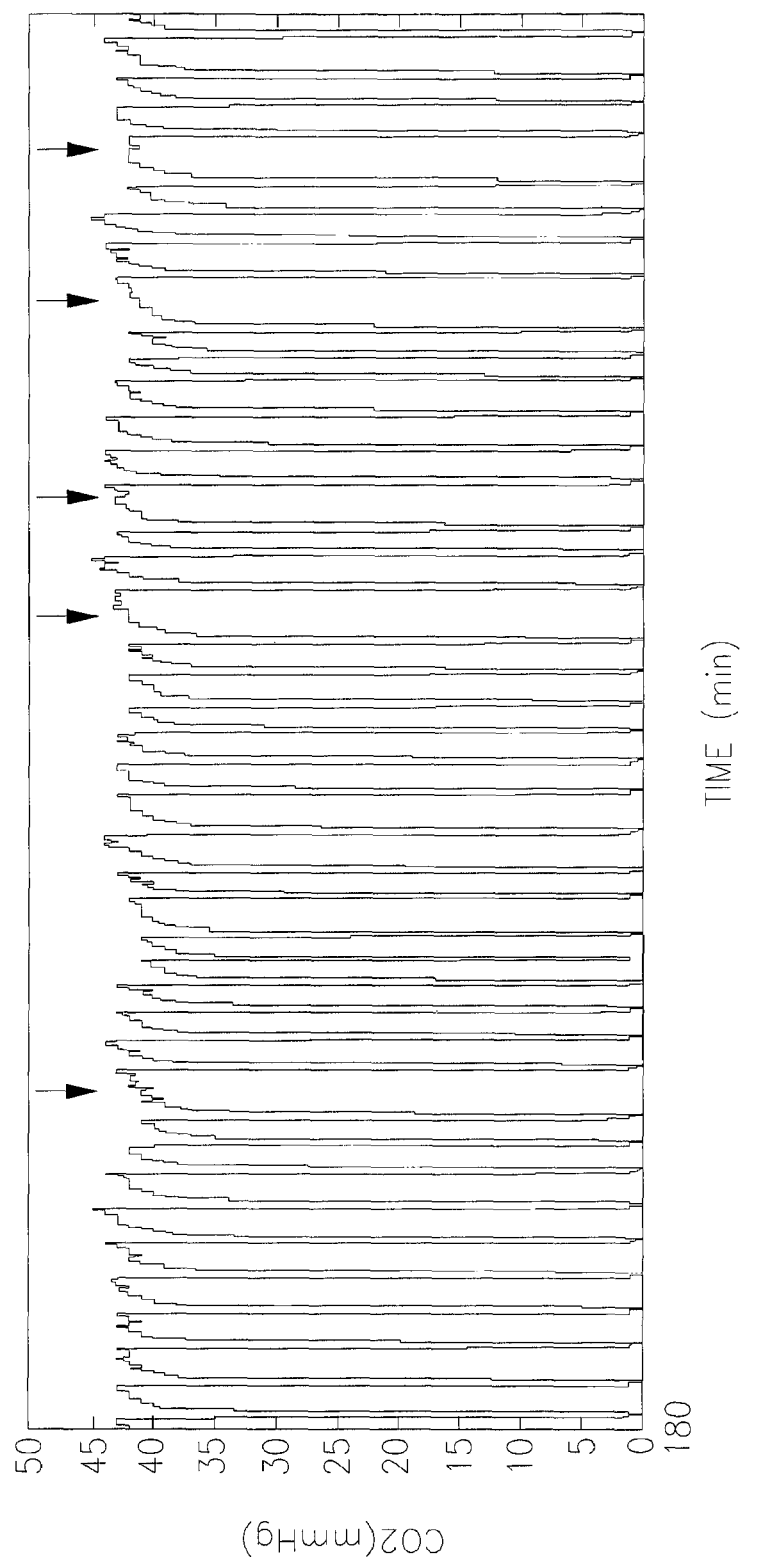
FIGS. 1A and B show series of $CO_2$ waveforms in a weaning patient, according to some embodiments of the invention.
Figure 1B:
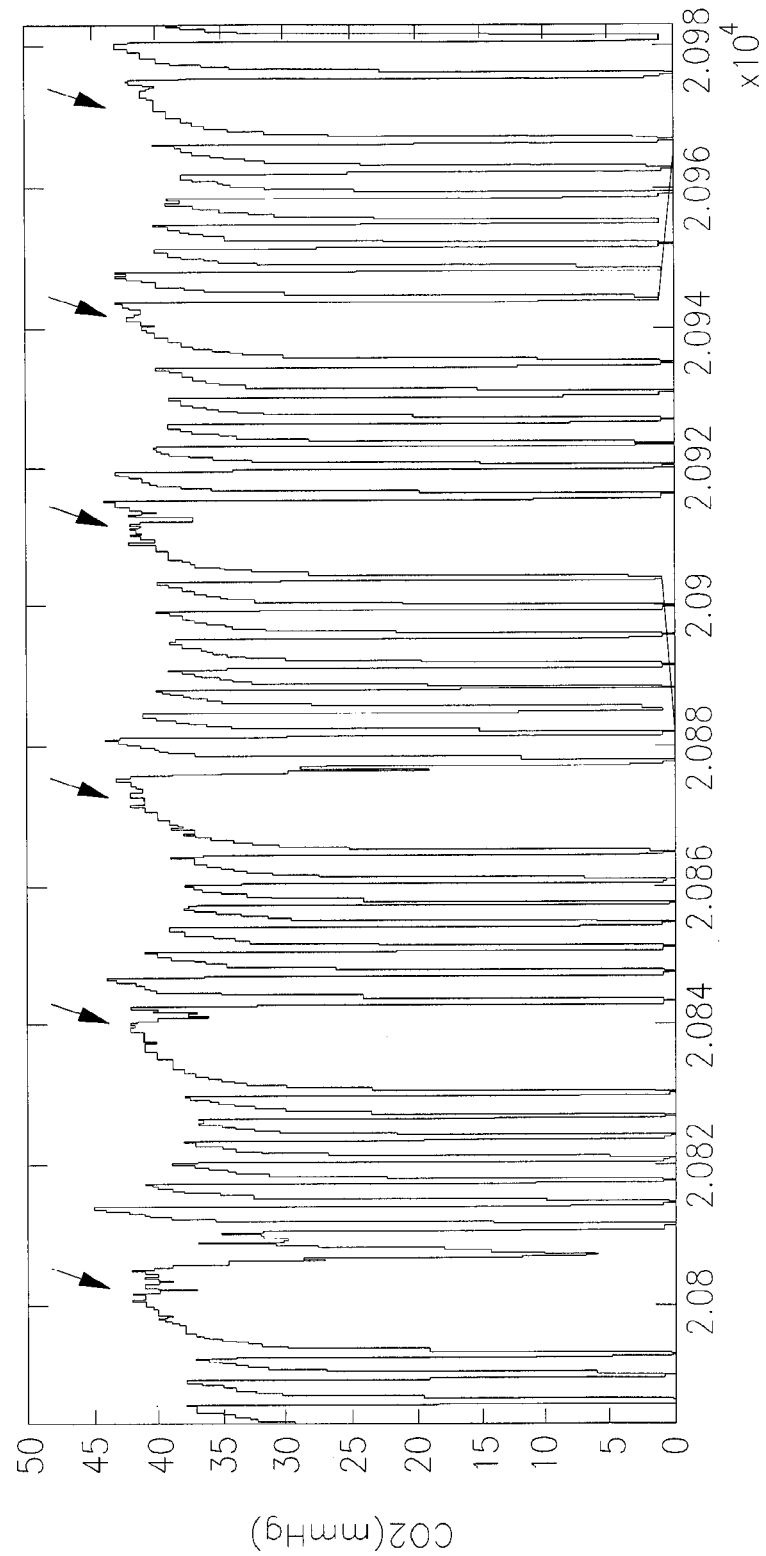
Figure 2:
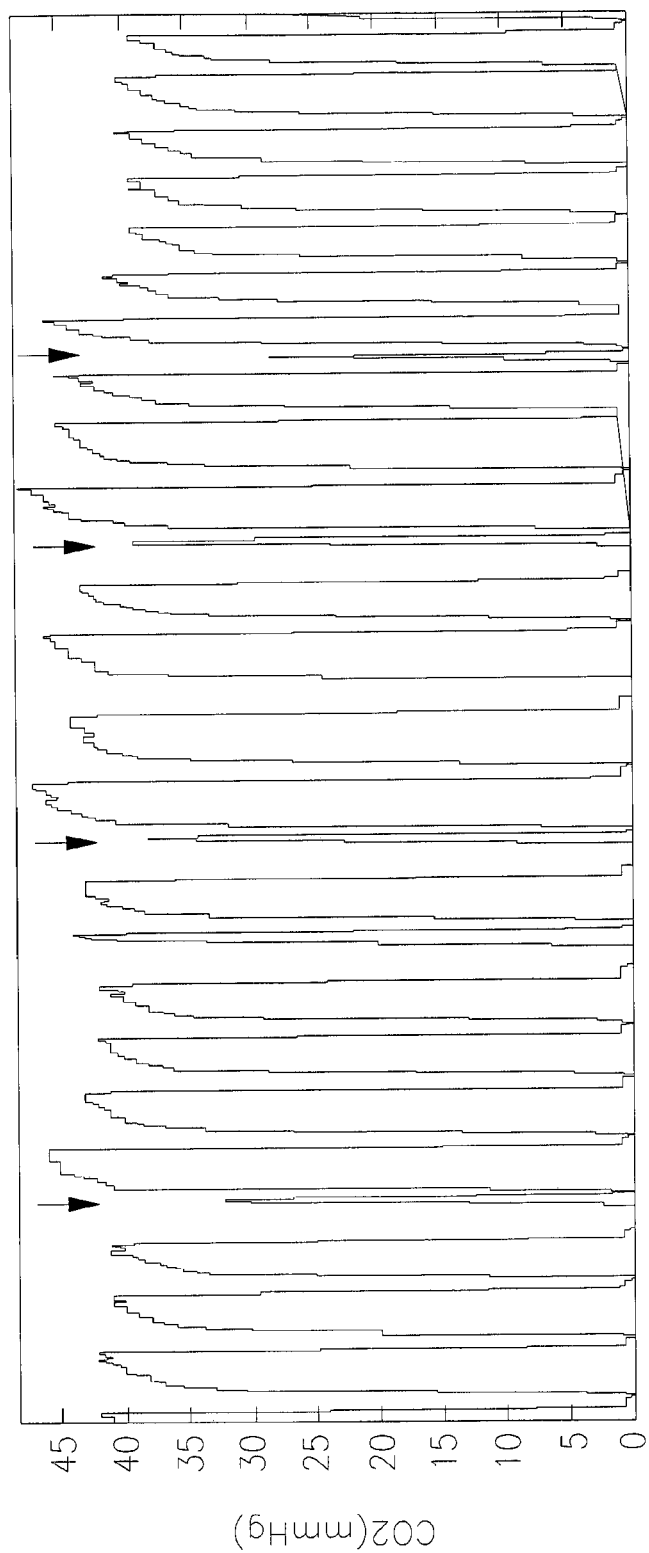
FIG. 2 shows a series of $CO_2$ waveforms in a weaning patient, according to some embodiments of the invention.
Figure 3A:
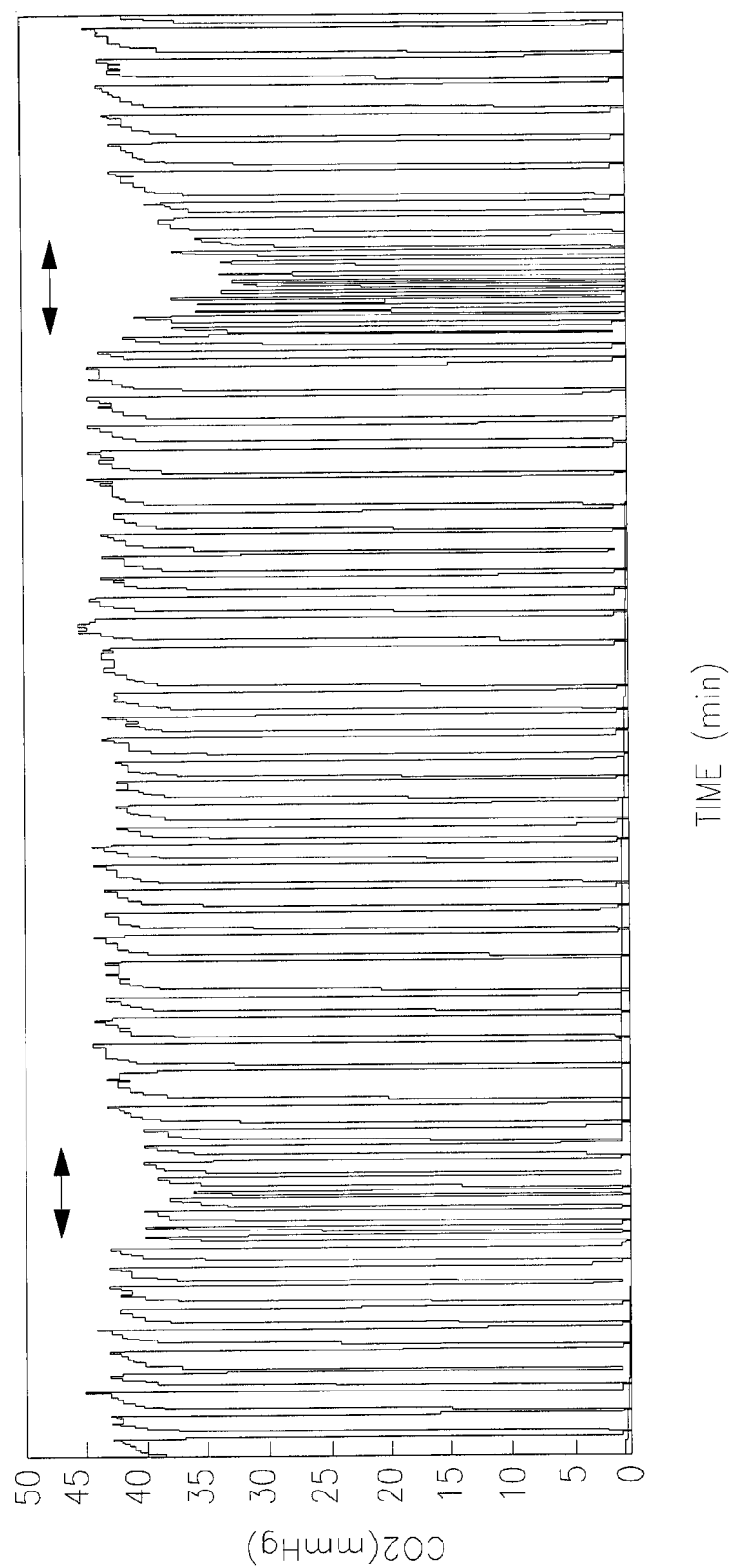
FIGS. 3A and B show series of $CO_2$ waveforms in a weaning patient, according to some embodiments of the invention.
Figure 3B:
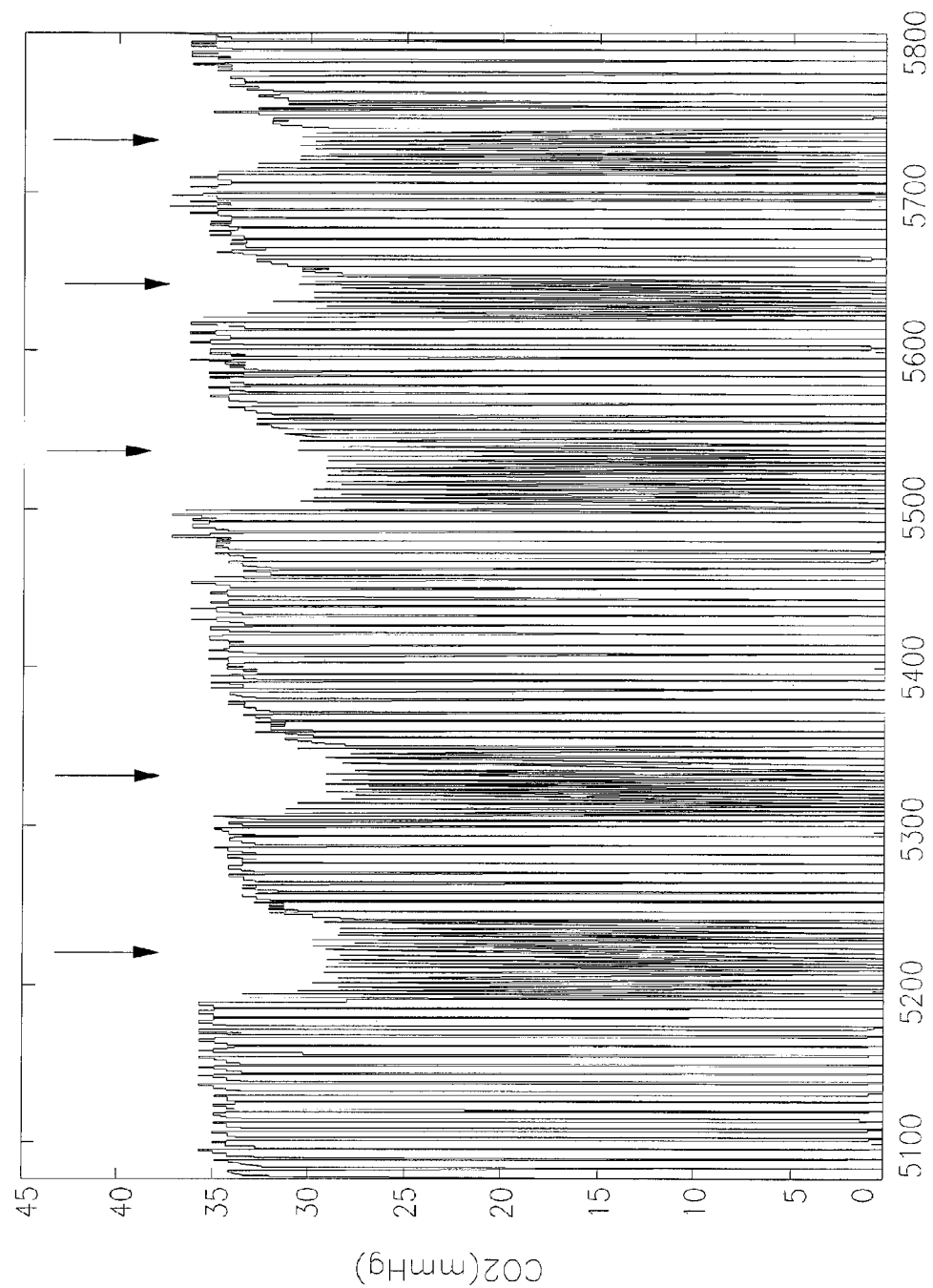

FIGS. 1-3 show series of $CO_2$ waveforms of weaning patients, according to some embodiments of the invention. In each one of FIGS. 1-3 the distinct patterns (FIG. 1: "sigh events", FIG. 2. "spike events" and FIG. 3 "pools") are marked by arrows and can easily be observed among the "regular" breaths.

Figure 4:
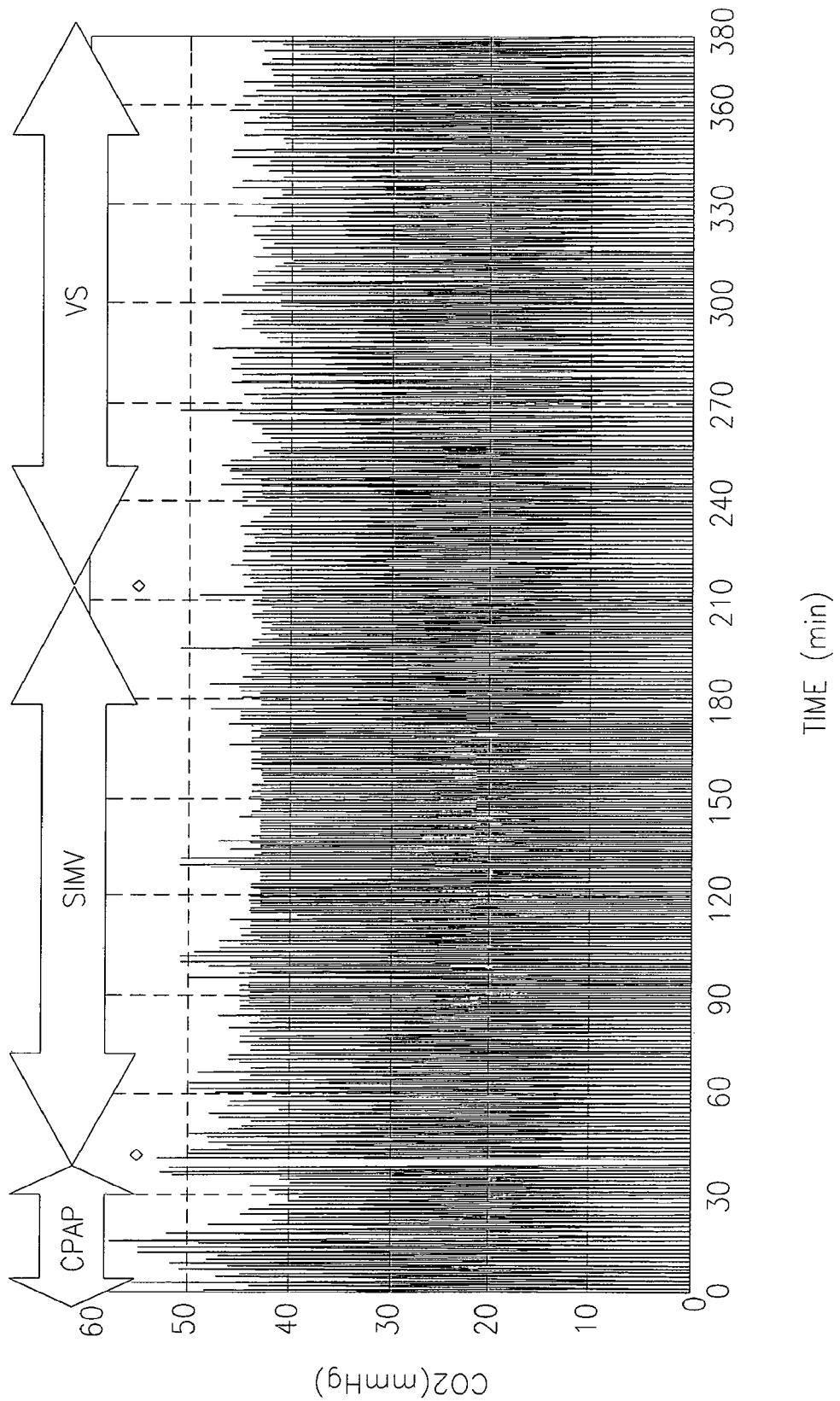
FIG. 4 shows a series of $CO_2$ waveforms in different ventilation modes (CPAP, SIMV and VS), according to some embodiments of the invention.

The patterns appear in different frequencies during weaning, at different modes of ventilation (CPAP, SIMV and VS), as shown in FIG. 4. The arrows indicate the ventilation mode at that time.

Figure 5:
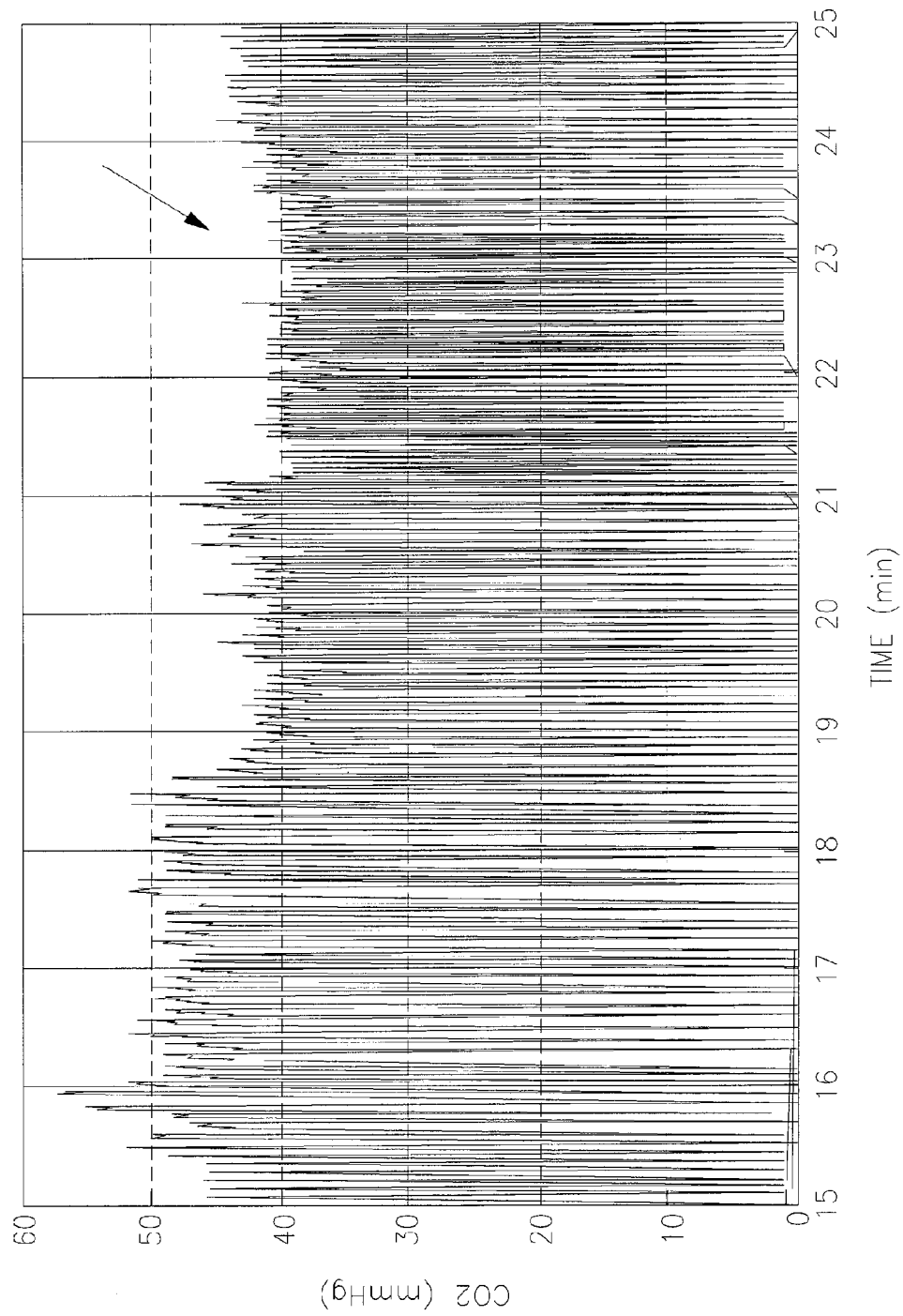
FIG. 5 shows a "zoom-in" series of $CO_2$ waveforms taken from the CPAP section of FIG. 4, according to some embodiments of the invention.

FIG. 5 shows a "zoom-in" series of $CO_2$ waveforms taken from the CPAP section of FIG. 4, according to some embodiments of the invention. The deterioration of the patient's condition with time, during CPAP ventilation can clearly be seen by the higher frequency of "pools" (see arrow).

Figure 6:
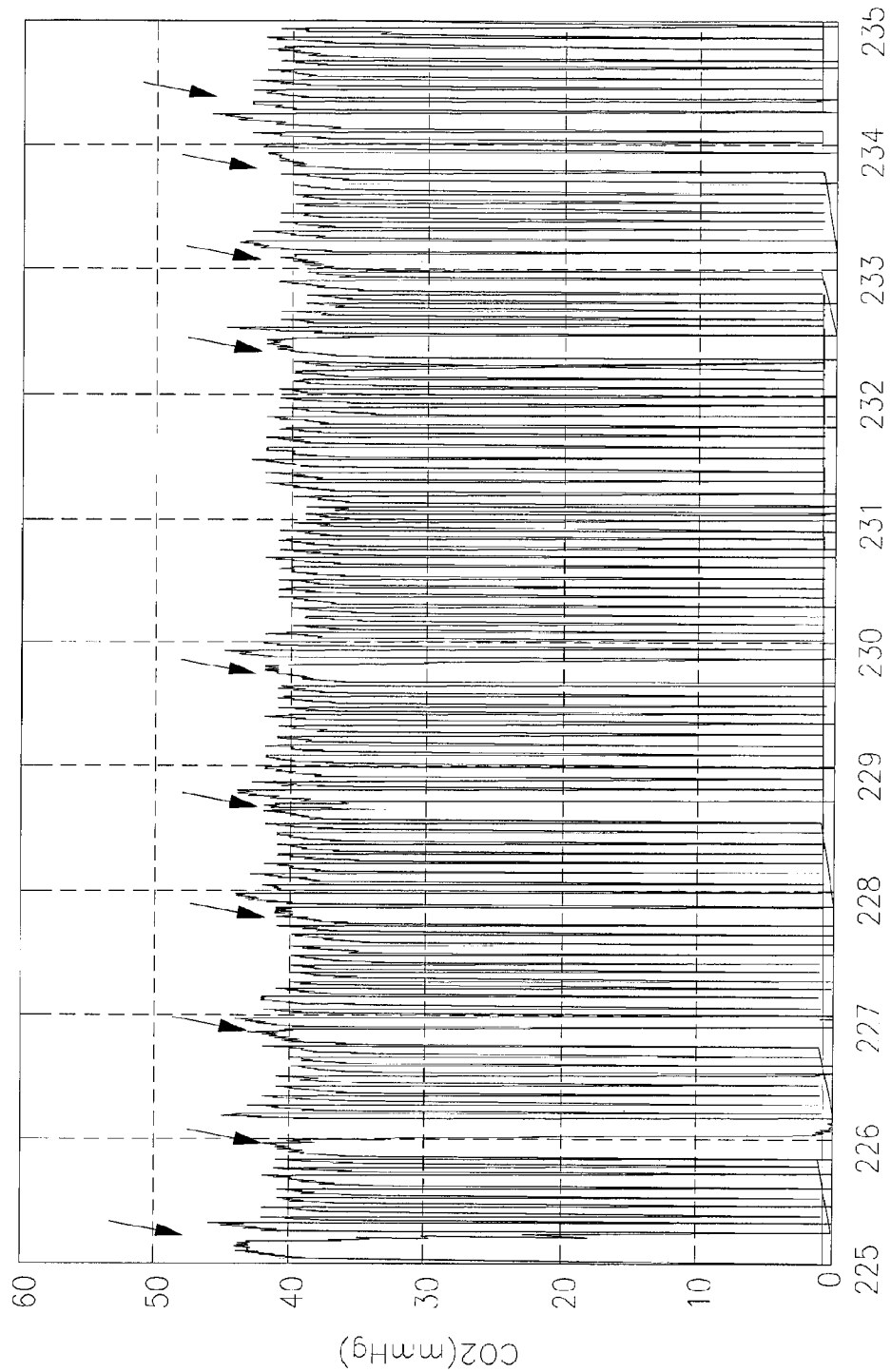
FIG. 6 shows a "zoom-in" series of $CO_2$ waveforms taken a few minutes after starting the VS section of FIG. 4, according to some embodiments of the invention.

FIG. 6 shows a "zoom-in" series of $CO_2$ waveforms taken a few minutes after starting the VS section of FIG. 4, according to some embodiments of the invention. The "sigh events" are marked be arrows.

Figure 7:
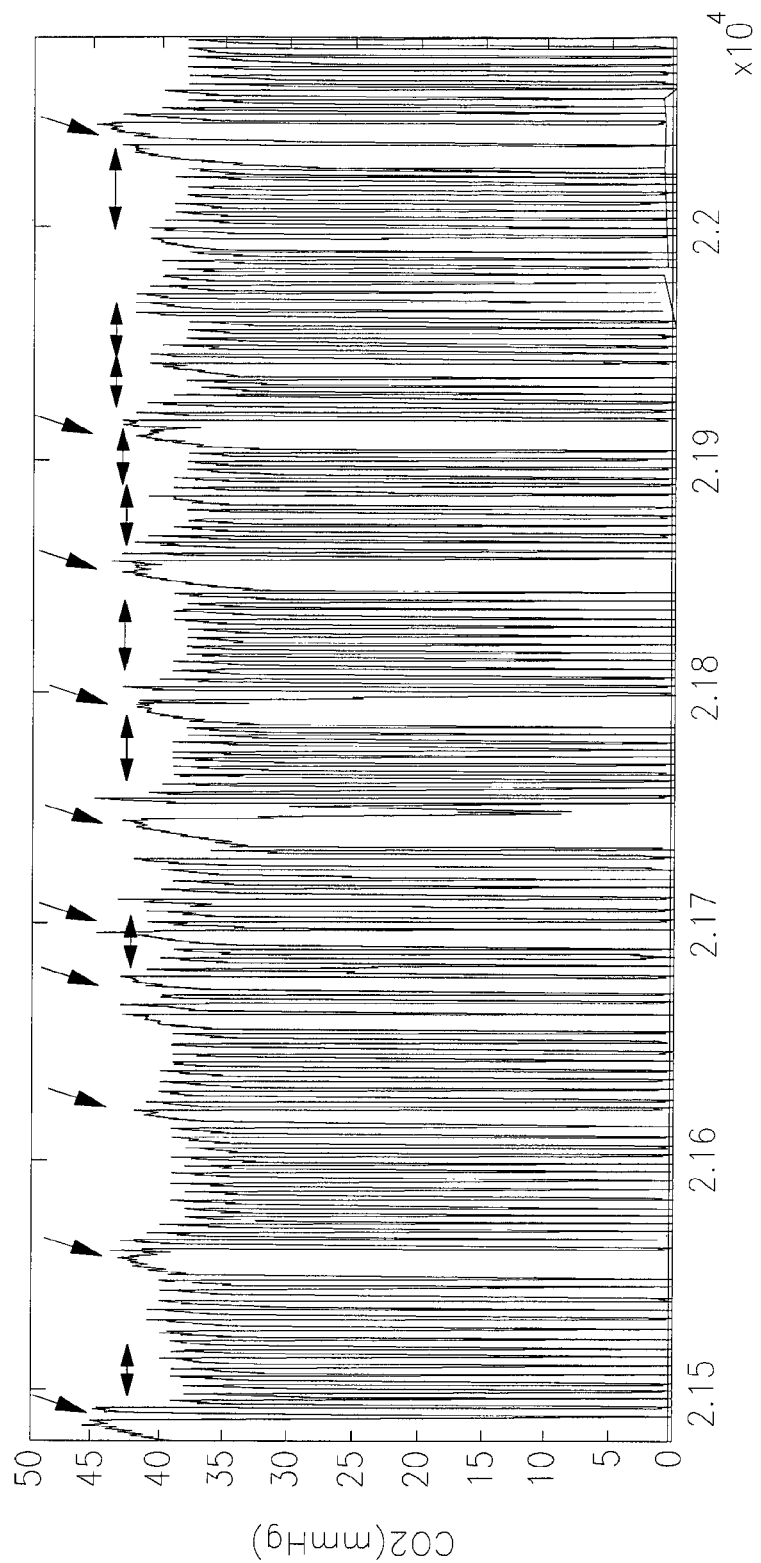
FIG. 7 shows a "zoom-in" series of $CO_2$ waveforms taken from the VS section of FIG. 4, according to some embodiments of the invention.

FIG. 7 shows a "zoom-in" series of $CO_2$ waveforms taken from the VS section of FIG. 4, according to some embodiments of the invention. The deterioration of the patient's condition with time, during VS can clearly be seen by the higher frequency of "pools" (marked be horizontal arrows) in addition to the "sigh events" (marked be arrows).

It is also noted that the some of the characteristics (for example, the pooling effect) occurred together with changes in the Respiration Rate.

The appearance of the distinct patterns (for example, the "sigh events", "spike events" and "pools"), their frequencies and extent, could serve as indicators for progress of the weaning process. Of course, the three distinct patterns disclosed herein are merely examples and other distinct patterns (characteristics) that appear in the $CO_2$ waveforms or waveforms series may also be indicative to the progress and effectiveness of the weaning process.

According to some embodiments, the appearance of $CO_2$ distinct patterns their frequencies and/or extent, optionally together with additional ventilator parameter (such as venti-lation modes, tidal volume, minute ventilation, and PEEP (Positive End-Expiratory Pressure)) may serve as indicators to the progress and effectiveness of the weaning process.

The appearance of the $CO_2$ distinct patterns, their frequencies and/or extent, together with additional ventilator parameter (such as ventilation modes, tidal volume, minute ventilation and PEEP) may also serve as indicators for ventilation related conditions such as air-leaks, a-synchrony, rebreathing, changes in compliance, obstruction and triggering effort.

Referring to the term "a-synchrony": During weaning the patient breath spontaneous breaths and the ventilator "helps" by "filling in" and adding flow, for example, or in other ways (depending on the ventilator mode). A-synchrony is when the settings of the ventilator are such that it interferes with the spontaneous breathing. For example, the patient tries to start a new breath in the middle of a ventilator breath.

Referring to the term "Rebreathing": breathing a new breath without finishing the previous breath.

What we claim is:

1. A method for monitoring effectiveness of weaning of a subject from a respiratory ventilator, the method comprising:
    obtaining a series of $CO_2$ waveforms from expired breath of a subject undergoing respiratory ventilation weaning;
    identifying a distinct pattern in the series of $CO_2$ waveforms;
    determining a frequency and/or an extent of the distinct pattern in the series of $CO_2$ waveforms; and
    providing an indication relating to the effectiveness of the weaning process, based on the determined frequency and/or extent of the distinct pattern;
    wherein an increase in the frequency and/or the extent of the distinct pattern, as compared to a baseline, is indicative of a deterioration in the weaning effectiveness.

2. The method of claim 1, wherein said distinct pattern is selected from a group consisting of "sigh events", "spike events" and "pools".

3. The method of claim 1, further comprising providing a signal to a ventilator at least partially based on the determined frequency and/or extent of the distinct patterns in the series of $CO_2$ waveforms and thus inducing a change in one or more parameters of the ventilator.

4. The method of claim 3, wherein said change in one or more parameters of the ventilator comprises a change in the level of support to the ventilation, allowing the patient to rest from weaning attempts, changing a mode/program of weaning or any combination thereof.

5. The method of claim 3, wherein providing a signal to the ventilator is further based on one or more additional parameters selected from the group consisting of: age of the subject, medical condition of the subject, medical history of the subject and medications administered to the subject.

6. The method of claim 3, wherein providing a signal to the ventilator is further based on one or more additional parameters selected from the group consisting of: respiration rate, tidal volumes, minute ventilation (the total lung ventilation per minute), inspiration rate and expiration rate at ambient pressure in the absence of ventilator assistance, ventilator mode and ventilator setup parameters.

7. The method of claim 1, wherein characterizing distinct patterns in a series of $CO_2$ waveforms comprises segmenting the series of $CO_2$ waveforms into breaths (waveforms), and calculating for each breath one or more features.

8. The method of claim 1, wherein the one or more features comprise: area under the curve (AUC), breath duration (inhalation, expiration or both), I to E ratio, maximal $CO_2$ value, minimal $CO_2$ value or any combination thereof.

9. The method of claim 1, wherein characterizing distinct patterns in the series of $CO_2$ waveforms comprises determining the ratios between the distinct patterns.

\* \* \* \* \*